(12) United States Patent
Jaeger et al.

(10) Patent No.: US 10,273,285 B2
(45) Date of Patent: Apr. 30, 2019

(54) FUSION PROTEINS AND USES THEREOF

(71) Applicant: MORPHOSYS AG, Planegg (DE)

(72) Inventors: Sebastian Jaeger, Gräfelfing (DE);
Daniela Daubert, Olching (DE);
Kathrin Goetz, Westendorf (DE)

(73) Assignee: MORPHOSYS AG, Planegg (DE)

( * ) Notice: Subject to any disclaimer, the term of this patent is extended or adjusted under 35 U.S.C. 154(b) by 149 days.

(21) Appl. No.: 15/319,434

(22) PCT Filed: Jun. 9, 2015

(86) PCT No.: PCT/EP2015/062833
§ 371 (c)(1),
(2) Date: Dec. 16, 2016

(87) PCT Pub. No.: WO2015/193143
PCT Pub. Date: Dec. 23, 2015

(65) Prior Publication Data
US 2017/0121388 A1    May 4, 2017

(30) Foreign Application Priority Data
Jun. 18, 2014  (EP) .................................... 14172950

(51) Int. Cl.
| | | |
|---|---|---|
| *C07K 14/715* | (2006.01) | |
| *C07K 14/005* | (2006.01) | |
| *C12N 7/00* | (2006.01) | |
| *C12N 15/62* | (2006.01) | |
| *C12N 15/86* | (2006.01) | |
| *C07K 14/705* | (2006.01) | |
| *A61K 39/00* | (2006.01) | |

(52) U.S. Cl.
CPC ........ *C07K 14/7158* (2013.01); *C07K 14/005* (2013.01); *C07K 14/705* (2013.01); *C12N 7/00* (2013.01); *C12N 15/62* (2013.01); *C12N 15/86* (2013.01); *A61K 39/00* (2013.01); *C07K 2319/00* (2013.01); *C07K 2319/40* (2013.01); *C12N 2740/13023* (2013.01); *C12N 2740/16023* (2013.01); *C12N 2810/855* (2013.01)

(58) Field of Classification Search
CPC .............. C07K 14/005; C07K 14/7158; C07K 2319/00; C12N 15/62; C12N 15/86; C12N 7/00; C12N 2810/855; C12N 2740/13023; C12N 2740/16023
See application file for complete search history.

(56) References Cited

U.S. PATENT DOCUMENTS 7,763,258 B2    7/2010  Doms et al. ............... 424/199.1

FOREIGN PATENT DOCUMENTS

| EP | 15729781.3 | 3/1917 |
| EP | 0449116 B1 | 8/1999 |
| WO | WO 2005/042695 A2 | 5/2005 |
| WO | WO 2005/068639 A2 | 7/2005 |
| WO | WO 2006/032674 A1 | 3/2006 |
| WO | WO 2007/054792 A1 | 5/2007 |
| WO | WO2008/089144 | 7/2008 |
| WO | WO2013/068847 | 5/2013 |
| WO | WO2014/128568 | 8/2014 |

OTHER PUBLICATIONS

Delachambre et al. "The GAG Precursor of Simian Immunodeficiency Virus Assembles into Virus-like Particles" 1989 The Embo Journal (8)9:2653-2660.
Deml et al. "Increased Incorporation of Chimeric Human Immunodeficiency Virus Type 1 gp120 Proteins into Pr55$^{gag}$ Virus-like Particles by an Epstein-Barr Virus gp220/350-Derived Transmembrane Domain" 1997 Virology 235:10-25.
Kaczmarczyk et al. "Protein Delivery Using Engineered Virus-like Particles" 2011 Proceedings of the National Academy of Sciences 108 (41):16998-17003.
Mayr, L. "Virus-like Particles (VLPs) as a Novel and Effective Display System and Effective Display System for Intramembrane Protein" 8th Annual PEGS Conference, Boston, Apr. 30-May 4, 2012.
Tissot et al. "Versatile Virus-like Particle Carrier for Epitope Based Vaccines" 2010 PLOS ONE 5(3):e9809.
International Search Report from PCT/EP2015/062833 dated Sep. 23, 2015.
International Preliminary Report on Patentability from PCT/EP2015/062833 dated Dec. 20, 2016.
Extended European Search Report from EP 14172950 dated Dec. 16, 2014.

*Primary Examiner* — Robert S Landsman
(74) *Attorney, Agent, or Firm* — Licata & Tyrrell P.C.

(57) ABSTRACT

The present disclosure relates to fusion proteins that are highly useful for the generation of virus-like particles for the display of membrane spanning proteins. Related embodiments, methods and uses are disclosed.

12 Claims, 3 Drawing Sheets

Specification includes a Sequence Listing.

SEQUENCE LISTING

<160> NUMBER OF SEQ ID NOS: 3

<210> SEQ ID NO 1
<211> LENGTH: 538
<212> TYPE: PRT
<213> ORGANISM: Moloney murine leukemia virus

<400> SEQUENCE: 1

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240
```

```
Asn Asn Pro Ser Phe Ser Glu Asp Pro Gly Lys Leu Thr Ala Leu Ile
            245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
            275                 280                 285

Glu Ala Arg Lys Ala Val Arg Gly Asp Asp Gly Arg Pro Thr Gln Leu
290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
            325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
            355                 360                 365

Leu Glu Arg Leu Lys Glu Ala Tyr Arg Arg Tyr Thr Pro Tyr Asp Pro
            370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
            405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
            435                 440                 445

Glu Glu Lys Glu Glu Arg Arg Arg Thr Glu Asp Glu Gln Lys Glu Lys
            450                 455                 460

Glu Arg Asp Arg Arg Arg His Arg Glu Met Ser Lys Leu Leu Ala Thr
465                 470                 475                 480

Val Val Ser Gly Gln Lys Asp Arg Gln Gly Gly Glu Arg Arg
            485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp
            530                 535

<210> SEQ ID NO 2
<211> LENGTH: 512
<212> TYPE: PRT
<213> ORGANISM: Human immunodeficiency virus (HIVB1)

<400> SEQUENCE: 2

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
            50                  55                  60

Gln Pro Ser Leu Gln Thr Gly Ser Glu Glu Leu Arg Ser Leu Tyr Asn
```

```
            65                  70                  75                  80
Thr Val Ala Thr Leu Tyr Cys Val His Gln Arg Ile Glu Ile Lys Asp
                    85                  90                  95

Thr Lys Glu Ala Leu Asp Lys Ile Glu Glu Gln Asn Lys Ser Lys
                100                 105                 110

Lys Lys Ala Gln Gln Ala Ala Asp Thr Gly His Ser Ser Gln Val
                115                 120                 125

Ser Gln Asn Tyr Pro Ile Val Gln Asn Ile Gln Gly Gln Met Val His
            130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
                275                 280                 285

Pro Lys Glu Pro Phe Arg Asp Tyr Val Asp Arg Phe Tyr Lys Thr Leu
                290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Thr Ala Thr Ile Met Met Gln Arg Gly Asn Phe Arg
            370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Tyr Lys Gly Arg Pro Gly Asn Phe
                435                 440                 445

Leu Gln Ser Arg Pro Glu Pro Thr Ala Pro Pro Phe Leu Gln Ser Arg
            450                 455                 460

Pro Glu Pro Thr Ala Pro Pro Glu Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495
```

```
Pro Leu Thr Ser Leu Arg Ser Leu Phe Gly Asn Asp Pro Ser Ser Gln
                500                 505                 510

<210> SEQ ID NO 3
<211> LENGTH: 360
<212> TYPE: PRT
<213> ORGANISM: Homo sapiens

<400> SEQUENCE: 3

Met Glu Asp Phe Asn Met Glu Ser Asp Ser Phe Glu Asp Phe Trp Lys
 1               5                  10                  15

Gly Glu Asp Leu Ser Asn Tyr Ser Tyr Ser Ser Thr Leu Pro Pro Phe
                20                  25                  30

Leu Leu Asp Ala Ala Pro Cys Glu Pro Glu Ser Leu Glu Ile Asn Lys
                35                  40                  45

Tyr Phe Val Val Ile Ile Tyr Ala Leu Val Phe Leu Leu Ser Leu Leu
 50                  55                  60

Gly Asn Ser Leu Val Met Leu Val Ile Leu Tyr Ser Arg Val Gly Arg
 65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
                100                 105                 110

Ile Phe Gly Thr Phe Leu Cys Lys Val Val Ser Leu Leu Lys Glu Val
                115                 120                 125

Asn Phe Tyr Ser Gly Ile Leu Leu Leu Ala Cys Ile Ser Val Asp Arg
                130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
                180                 185                 190

Ser Pro Ala Cys Tyr Glu Asp Met Gly Asn Asn Thr Ala Asn Trp Arg
                195                 200                 205

Met Leu Leu Arg Ile Leu Pro Gln Ser Phe Gly Phe Ile Val Pro Leu
                210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
                260                 265                 270

Ala Asp Thr Leu Met Arg Thr Gln Val Ile Gln Glu Thr Cys Glu Arg
                275                 280                 285

Arg Asn His Ile Asp Arg Ala Leu Asp Ala Thr Glu Ile Leu Gly Ile
                290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335
```

```
Lys Asp Ser Leu Pro Lys Asp Ser Arg Pro Ser Phe Val Gly Ser Ser
            340                 345                 350

Ser Gly His Thr Ser Thr Thr Leu
        355                 360
```

FUSION PROTEINS AND USES THEREOF

This patent application is the National Stage of International Application No. PCT/EP2015/062833 filed Jun. 9, 2015, which claims the benefit of EP 14172950.9 filed Jun. 18, 2014 each of which is incorporated by reference in its entirety.

BACKGROUND OF THE INVENTION

Membrane proteins are the major group of targets for antibody therapeutics. Integral membrane proteins, such as G protein-coupled receptors (GPCRs), ion channels and transporters, are involved in diverse biological functions and also in many diseases. Approximately 40% of all modern medical drugs target GPCRs. However, due to their hydrophobic domains, membrane proteins are difficult to solubilize and to purify. Pure and stable protein samples of membrane proteins are hardly available. Therefore there is high need to provide technologies for the efficient presentation of membrane proteins in order to develop novel antibody-based therapeutics.

Retroviruses are enveloped particles of around 100 nm in size (Human Immunodeficiency Virus (HIV): ~120 nm, Moloney Murine Leukemia Virus (MoIMLV): ~90 nm). The virions contain two identical single-stranded RNA molecules of 7-10 kb in length. The envelope of the virus is acquired during the assembly of the virus at the plasma membrane and contains host cell phospholipids and proteins, but also some viral glycoproteins (in the case of HIV for example gp41 and gp120). The role of these viral envelope proteins is to identify and bind to receptor sites on target cells. After binding, the virus fuses with the target cell membrane, allowing the capsid and the viral genome to enter and infect the target/host cell. After infection of the host cell the virus uses its own reverse transcriptase to synthesize DNA from its RNA genome. The integrase enzyme inserts the DNA into the host cells genome. Afterwards, the host cell expresses the viral proteins required for assembly of new copies of the virus.

As one example, the HIV DNA contains 3 main genes (gag, pol, env) and 6 accessory genes (vif, vpr, vpu, tat, rev, nef). The three main genes contain information needed to make the structural proteins for new virus particles. ENV encodes the viral envelope protein gp160, which is cleaved by furin to form gp120 and gp41. These are transported to the plasma membrane of the host cell, where gp41 anchors gp120 to the membrane of the infected cell. POL encodes the enzymes required for replication (reverse transcriptase) and integration (integrase) of the virus as well as a viral protease. Gag is a multi-domain polyprotein. The Gag polyprotein is cleaved by the viral protease separating six proteins: the three folded domains matrix (MA), capsid (CA) and nucleocapsid (NC) and three shorter peptides SP1, SP2 and p6. The accessory genes encode for regulatory proteins that control the ability of HIV to infect cells, produce new copies of virus (replicate), or cause disease.

The assembly of the virus occurs at the host cell plasma membrane, into which the viral envelope proteins were inserted. The gag proteins, the major part of the viral capsid (2000-4000 copies per virion), associate with the inner surface of the plasma membrane. Gag recruits other essential virion components including the viral replication proteins (expressed as Gag-Pol fusion proteins) and the genomic RNA. Assembly of the Gag proteins leads to the budding of the virus, which is initially a noninfectious virion. This so-called immature virion mainly contains uncleaved Gag polyproteins. Formation of an infectious virion requires processing of Gag by the viral protease at five specific sites, leading to a rearrangement of the interior organization.

Virus-like particles (VLPs) resemble viruses but are non-infectious because they do not contain any viral genetic material. The expression of viral structural proteins results in the self-assembly of virus like particles (VLPs). Different strategies exist for the generation of VLPs. VLPs can be produced in a variety of cell culture systems including mammalian cell lines, insect cell lines, yeast, and plant cells.

Principally, the recombinant over-expression of Gag is sufficient for the formation of virus-like particles. The Gag proteins associate with the inner surface of the plasma membrane causing the budding of empty shells into the cell culture medium. The empty shell is surrounded by plasma membrane of the host cell and contains various host cell proteins.

Viral major capsid proteins, such as the HIV GAG-protein, are known tools for the generation of virus-like particles (VLPs) (Delachambre, 1989, Deml 1997). Such VLPs can be used for the expression of heterologous proteins, in particular proteins which are difficult to express by other means, for example membrane spanning protein. See for example U.S. Pat. No. 7,763,258. However, these systems are characterized by the co-expression of the viral capsid protein and the heterologous membrane spanning protein.

Viral major capsid proteins have also been used to generate vaccines. See for example EP0449116 or WO07/054792. In such approaches, the capsid proteins were modified to incorporate certain heterologous proteins which are presented to the immune system on said capsid proteins. Also bacteriophage coat proteins were used to generate antigen-presenting phage-derived particles for vaccination (WO06/032674). However, such phage-derived particles are produced in E. coli, and are therefore not surrounded by plasma membrane of a eukaryotic cell.

Virus-like particles have also been generated utilizing other proteins than viral capsid proteins for the presentation of peptides or proteins on the virus-like particles. Such proteins include neuraminidase (NA) and hemmagglutinin (HA) (Kaczmarczyk et al. (PNAS) 108, 16998-17003).

Other systems utilize protein-protein interaction techniques in which both, the capsid protein and the protein of interest, are fused to a partner peptidic or proteinaceous moiety, which interact with each other. This leads to the co-localization of the capsid protein with the protein of interest, and hence the protein of interest may be presented or displayed on a VLP. See Mayr & Schenker (presentation on the 8th PEGS Annual Conference, Boston, Apr. 30-May 3, 2012).

The present disclosure provides an improved method for the presentation and display of proteins, in particular, transmembrane proteins, on virus-like particles.

Importantly, the present disclosure makes use of fusion proteins, in which the protein that is to be displayed is N-terminally fused to the viral capsid protein. Viral capsid proteins are N-terminally myristoylated, and therefore the prior art did not use such N-terminal fusions. In the present disclosure it is shown, that such fusion proteins can however be successfully expressed and the respective protein of interest be presented in virus-like particles. Such a system has numerous advantages.

FIGURE LEGENDS

FIG. 1 shows the results of a Western Blot analyses. Panel A shows the results of Experiment A, panel B shows the result of Experiment B. For details see Example 3. The supernatants were probed with an anti-GAG antibody or an anti-GPCR antibody as indicated in the Figure. The right lanes in the blots shown in panel A comprise a pre-stained size marker. The same is true for the left lanes in the blots shown in panel B.

DETAILED DESCRIPTION OF THE INVENTION

Figure 1:
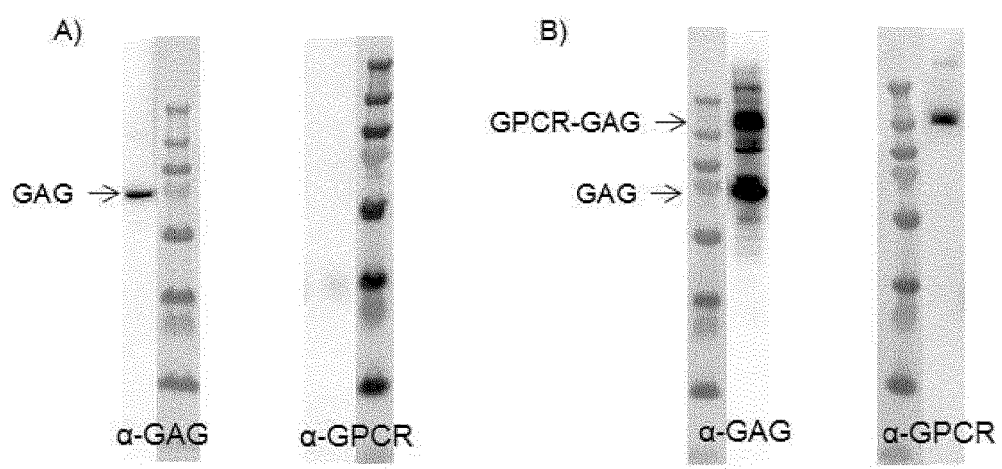

In certain embodiments the present disclosure relates to a fusion protein comprising a membrane protein N-terminally fused to a viral major capsid protein.

The term "fusion protein" refers to a hybrid protein expressed by a nucleic acid molecule comprising nucleotide sequences of at least two genes or two nucleic acid molecules that do not naturally occur together.

The term "membrane protein" refers to a protein that is attached to or associated with a membrane of a cell or an organelle. If a membrane protein spans the cell membrane then said protein may also be referred to as "integral membrane protein" or "transmembrane protein". Therefore in certain embodiments of the present disclosure the membrane protein which is N-terminally fused to the viral major capsid protein is an integral membrane protein. In other embodiments of the present disclosure the membrane protein which is N-terminally fused to the viral major capsid protein is a transmembrane protein.

The term "N-terminally fused" refers to a genetic fusion of a first and a second polypeptide/protein, wherein the first polypeptide/protein forms the N-terminal portion of the fusion protein. In certain embodiments of the present disclosure the membrane protein forms the N-terminal portion of the fusion protein. "GPCR" or "G-protein coupled receptor" are membrane proteins. The term refers to a large family of cell surface receptors with an assortment of ligands and diverse biological actions. The importance of GPCRs in cellular function, their diversity, and their accessibility to exogenous agents make them an important focus of research into disease processes and drug discovery. GPCR activation events are communicated to cell signaling pathways via GTP-binding I proteins (G proteins) associated with the intracellular domain of the receptor. GPCRs constitute the largest group of drug targets today, highlighting their importance in biological research and in disease pathways. However, GPCRs are structurally complex, spanning the cell membrane seven times. Removal from the cell membrane usually destroys the receptor's native structure in which it is maintained by the environment of the lipid bilayer. GPCRs are thus extremely difficult to purify and manipulate experimentally, and their study relies on whole cells or isolated cell membranes. GPCRs include, without limitation, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, histamine receptors, protease-activated receptors, rhodopsins and other G-protein coupled seven transmembrane segment receptors. GPCRs also include these GPCR receptors associated with each other as homomeric or heteromeric dimers or as higher-order oligomers.

Exemplary GPCRs include: 5-HT1A, 5-HT1B, 5-HT1 D, 5-HT1E, 5-HT1F, 5-HT2A, 5-HT2B, 5-HT2C, 5-HT4, 5-HT5A, 5-HT6, 5-HT7, MI, M2, M3, M4, M5, AI, A2A, A2B, A3, aIA, aIB, aID, a2A, a2B, a2C, bI, b2, b3, ATI, AT2, BBI, BB2, BB3, BI, B2, CBI, CB2, CXCRI, CXCR2, CXCR3, CXCR4, CXCR5, CXCR6, CCR1, CCR2, CCR3, CCR4, CCR5, CCR6, CCR7, CCR8, CCR9, CCRIO, CX3CR1, XCRI, CCKI, CCK2, DI, D2, D3, D4, D5, ETA, ETB, GALI, GAL2, GAL3, motilin, ghrelin, HI, H2, H3, H4, CysLTI, CysLT2, BLTI, BLT2, OXE, ALX, LPAI, LPA2, LPA3, SIPI, S1P2, S1P3, S1P4, S1P5, MCHI, MCH2, MCI, MC2, MC3, MC4, MC5, NMUI, NMU2, YI, Y2, Y4, Y5, NTSI, NTS2, d, k, m, NOP, OXI, 0X2, P2Y1, P2Y2, P2Y4, P2Y6, P2Y11, PAF, PKRI, PKR2, PRRP, DP, EPI, EP2, EP3, EP4, FP, IPI, TP, PAR1, PAR2, PAR3, PAR4, sst2, sst5, sst3, sstI, sst4, NKI, NK2, NK3, TRH, UT, OT, VIA, V2, VIB, APJ, FFAI, FFA2, FFA3, GPBA, TSH, LH, FSH, GnRH, KiSSI, MTI, MT2, NPFFI, NPFF2, NPS, NPBWI, NPBW2, P2Y12, P2Y13, QRFP, RXFPI, RXFP2, RXFP3, RXFP4, TAI, TA3, TA4 and TA5.

In certain embodiments of the present disclosure the membrane protein which is N-terminally fused to the viral major capsid protein is a GPCR. In other embodiments of the present disclosure said GPCR is selected from the list of CCR1, CXCR1, CXCR2, CXCR4, CXCR5, CXCR7, motilin, ghrelin, PAR1 and PAR2. In other embodiments of the present disclosure said GPCR is CXCR2.

"Ion channels" are membrane proteins. The term refers to a protein crossing the lipid bilayer of a cell, which, in a regulated manner, transports solutes and/or water across cell membranes. Channels are responsible for generating and propagating electrical impulses in excitable tissues in the brain, heart, and muscle, and for setting the membrane potential of excitable and non-excitable cells. Exemplary ion channels include sodium channels, potassium channels, and calcium channels, as well as ligand gated ion channels such as serotonin, glutamate, and γ-aminobutyric acid (GABA) channels.

In certain embodiments of the present disclosure the membrane protein which is N-terminally fused to the viral major capsid protein is an ion channel.

The term "major capsid protein" or "capsid protein" refers to a viral protein or a functional equivalent thereof, which directs the assembly and the release of virus particles from the infected host cell. In certain embodiments of the present disclosure the major capsid protein or capsid protein is a retroviral capsid protein. In a preferred embodiment the major capsid protein or capsid protein is a Gag protein or a functional equivalent thereof.

The capsid protein may be a Gag protein. The term "Gag protein", "GAG protein" or "group-specific antigen" refers to a family of glycoproteins that form the capsid of certain viruses.

Two specific Gag proteins that may be used in accordance with the present disclosure include:

The Gag protein of Moloney murine leukemia virus (MoMLV)-(UniPort: P03332):

(SEQ ID NO.: 1)
MGQTVTTPLSLTLGHWKDVERIAHNQSVDVKKRRWVTFCSAEWPTFNVGW

PRDGTFNRDLITQVKIKVFSPGPHGHPDQVPYIVTWEALAFDPPPWVKPF

-continued

```
VHPKPPPPLPPSAPSLPLEPPRSTPPRSSLYPALTPSLGAKPKPQVLSDS

GGPLIDLLTEDPPPYRDPRPPPSDRDGNGGEATPAGEAPDPSPMASRLRG

RREPPVADSTTSQAFPLRAGGNGQLQYWPFSSSDLYNWKNNNPSFSEDPG

KLTALIESVLITHQPTWDDCQQLLGTLLTGEEKQRVLLEARKAVRGDDGR

PTQLPNEVDAAFPLERPDWDYTTQAGRNHLVHYRQLLLAGLQNAGRSPTN

LAKVKGITQGPNESPSAFLERLKEAYRRYTPYDPEDPGQETNVSMSFIWQ

SAPDIGRKLERLEDLKNKTLGDLVREAEKIFNKRETPEEREERIRRETEE

KEEERRTEDEQKEKERDRRRHREMSKLLATVVSGQKQDRQGGERRRSQLD

RDQCAYCKEKGHWAKDCPKKPRGPRGPRPQTSLLTLDD
```

The Gag protein of Human immunodeficiency virus (HIVB1)-(UniPort: P03347):

(SEQ ID NO.: 2)
```
MGARASVLSGGELDRWEKIRLRPGGKKKYKLKHIVWASRELERFAVNPGL

LETSEGCRQILGQLQPSLQTGSEELRSLYNTVATLYCVHQRIEIKDTKEA

LDKIEEEQNKSKKKAQQAAADTGHSSQVSQNYPIVQNIQGQMVHQAISPR

TLNAWVKVVEEKAFSPEVIPMFSALSEGATPQDLNTMLNTVGGHQAAMQM

LKETINEEAAEWDRVHPVHAGPIAPGQMREPRGSDIAGTTSTLQEQIGWM

TNNPPIPVGEIYKRWIILGLNKIVRMYSPTSILDIRQGPKEPFRDYVDRF

YKTLRAEQASQEVKNWMTETLLVQNANPDCKTILKALGPAATLEEMMTAC

QGVGGPGHKARVLAEAMSQVTNTATIMMQRGNFRNQRKMVKCFNCGKEGH

TARNCRAPRKKGCWKCGKEGHQMKDCTERQANFLGKIWPSYKGRPGNFLQ

SRPEPTAPPFLQSRPEPTAPPEESFRSGVETTTPPQKQEPIDKELYPLTS

LRSLFGNDPSSQ
```

In certain embodiments the present disclosure relates to a fusion protein comprising a membrane protein N-terminally fused to a viral major capsid protein, wherein said viral major capsid protein is a GAG protein. In certain embodiments said Gag protein is a Gag protein of Moloney murine leukemia virus. In certain embodiments said Gag protein is a Gag protein of Human immunodeficiency virus.

It is also possible to utilize only a part of a viral major capsid protein, such as a GAG protein. In such cases the membrane protein is N-terminally fused to a part of a viral major capsid protein or to a part of a GAG protein.

Therefore, in certain embodiments the present disclosure provides a fusion protein comprising a membrane protein N-terminally fused to a part of a viral major capsid protein. In other embodiments the present disclosure provides a fusion protein comprising a membrane protein N-terminally fused to a functional part of a viral major capsid protein. In other embodiments the present disclosure provides a fusion protein comprising a membrane protein N-terminally fused to a part of a GAG protein. In other embodiments the present disclosure provides a fusion protein comprising a membrane protein N-terminally fused to a functional part of a GAG protein. In certain embodiments the present disclosure relates to a fusion protein comprising a membrane protein N-terminally fused to a viral major capsid protein. In other embodiments the fusion protein comprises a linker peptide between said membrane protein and said viral major capsid protein.

In certain embodiments the fusion protein of the present disclosure is capable of being incorporated or encapsulated into virus-like particles. In other embodiments the fusion protein of the present disclosure are incorporated or encapsulated into virus-like particles.

In certain embodiments the present disclosure relates to nucleic acid molecules encoding the fusion proteins of the present invention.

In certain embodiments the present disclosure relates to a vector comprising the nucleic acid molecule encoding the fusion proteins of the present invention.

The term "vector" refers to a polynucleotide molecule capable of transporting another polynucleotide to which it has been linked. Preferred vectors are those capable of autonomous replication and/or expression of nucleic acids to which they are linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and mammalian vectors). Other vectors can be integrated into the genome of a host cell upon introduction into the host cell, and thereby are replicated along with the host genome. Vectors may be compatible with prokaryotic or eukaryotic cells. Prokaryotic vectors typically include a prokaryotic replicon which may include a prokaryotic promoter capable of directing the expression (transcription and translation) of the peptide in a bacterial host cell, such as *Escherichia coli* transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment. Preferred vector are mammalian vectors. Other preferred vectors are mammalian vectors comprising a CMV promoter.

In certain embodiments the present disclosure relates to a host cell comprising the nucleic acid molecules or the vector encoding the fusion proteins of the present invention. In certain embodiments of the present disclosure the host cell is a mammalian host cell. In other embodiments of the present disclosure the host cell is an HKB11 cell or a HEK cell. In yet other embodiments of the present disclosure the fusion protein expressed in said host cell is under the control of a CMV promoter.

The term "recombinant host cell" or "host cell" refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are eukaryotic host cells, such as mammalian host cells. Preferred eukaryotic host cells include yeast and mammalian cells including murine and rodents, preferably vertebrate cells such as a mouse, rat, monkey or human cell line, for example HKB11 cells, PER.C6 cells, HEK cells or CHO cells.

In certain embodiments the present disclosure relates to a virus-like-particle comprising a fusion protein of the present invention. In other embodiments the present disclosure relates to a virus-like-particle comprising a fusion protein wherein said fusion protein is displayed on the surface of said virus-like-particle.

The term "Virus-like particle" or "VLP" refers to a structure resembling a retrovirus particle or a retrovirus-like particle with an envelope composed of a lipid bilayer and membrane proteins. Typically the envelope of the virus-like particle contains plasma membrane and membrane proteins obtained from the eukaryotic host cell. In certain embodiments of the present disclosure the virus-like particles are non-replicative or non-infectious, preferably non-replicative and non-infectious. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. Typically, a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus coated with a lipid membrane known as the viral envelope. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of a viral capsid or a viral-capsid like structure with an inherent repetitive organization, wherein said structure is, typically, spherical. For example, the capsids of retroviruses have a spherical form.

In certain embodiments the present disclosure relates to a virus-like-particle comprising a fusion protein of the present invention, wherein the virus-like-particle was produced from a eukaryotic host cell.

In certain embodiments the present disclosure relates to a method for the generation of virus-like-particles comprising a fusion protein of the present invention. In another embodiment the present disclosure relates to a method for the generation of virus-like-particles said method comprising the steps:
(a) providing a vector encoding a fusion protein of the present invention,
(b) transfecting a eukaryotic host cell with a vector of step (a)
(c) purifying the VLPs form the supernatant.

The fusion proteins and the virus-like particles of the present disclosure have numerous uses. For example, the VLPs can be used to display the respective fusion protein. Such a display system can be used, for example, for screening or panning of antibody libraries. This may lead to the identification of antibodies which may not be generated by other means due to the absence of appropriate antigen material.

In other embodiments the present disclosure therefore relates to the use of the fusion proteins or the VLPs of the present invention for the selection of a moiety, such as an antibody, that is reactive with the GPCR- or ion-channel part of the fusion protein of the present invention.

In other embodiments the present disclosure provides a method to identify a binding moiety binding to a membrane protein, said method comprising the steps:

(a) providing a fusion protein of the present invention,
(b) generating VLPs comprising the fusion protein of step (a),
(c) contacting the VLPs of step (b) with an antibody library,
(d) washing the VLPs to remove those antibodies that did not bind the VLP, and
(d) selecting an antibody which is reactive with the membrane protein part of said fusion protein.

EXAMPLES

Example 1: Selection of GAG Proteins and Membrane Proteins

First, two exemplary GAG proteins were selected for the proof of concept experiments. The Gag proteins chosen are the Gag protein of Moloney murine leukemia virus (UniPort: P03332; SEQ ID NO.: 1) and the Gag protein of Human immunodeficiency virus (UniPort: P03347; SEQ ID NO.: 2).

As exemplary integral membrane proteins three GPCRs were chosen: GPCR 1, GPCR 2 and GPCR 3. GPCR 1 is CXCR2 (UniPort: P03347; SEQ ID NO.: 3):

```
                                        (SEQ ID NO.: 3)
MEDFNMESDSFEDFWKGEDLSNYSYSSTLPPFLLDAAPCEPESLEINKYF

VVIIYALVFLLSLLGNSLVMLVILYSRVGRSVTDVYLLNLALADLLFALT

LPIWAASKVNGWIFGTFLCKVVSLLKEVNFYSGILLLACISVDRYLAIVH

ATRTLTQKRYLVKFICLSIWGLSLLLALPVLLFRRTVYSSNVSPACYEDM

GNNTANWRMLLRILPQSFGFIVPLLIMLFCYGFTLRTLFKAHMGQKHRAM

RVIFAVVLIFLLCWLPYNLVLLADTLMRTQVIQETCERRNHIDRALDATE

ILGILHSCLNPLIYAFIGQKFRHGLLKILAIHGLISKDSLPKDSRPSFVG

SSSGHTSTTL.
```

Example 2: Generation of Constructs and Expression of Proteins

All cloning experiments were performed using standard technologies. Proteins were cloned in pMAX vectors for the expression in mammalian cells. Expression in these vectors is under the control of the CMV promoter. The constructs that were generated produced either:
(a) the GAG protein,
(b) the GPCR protein, or
a fusion protein, in which the GPCR protein is fused N-terminal to the GAG-protein.

Expression of the proteins and production of the VLPs was done under standard conditions in suspension cultures. Host cells used in the present experiments are HKB11 cells (ATCC; CRL-12568) and HEK cells (Life Technologies). In one set of experiments (Experiment A) the host cells were transfected with the following two vectors: one vector expressing GAG and one vector expressing the GPCR. In another set of experiments (Experiment B) the host cells were also transfected with two vectors. However, one vector expressed GAG and the other vector expresses the GPCR-GAG fusion protein.

Example 3: Purification of VLPs and Analyses

Three days post transfection the supernatants containing the VLPs were harvested and purified using standard procedures (including precipitation and ion exchange chromatography). The proteins isolated were then subjected to Western Blot analysis and SDS-PAGE chromatography.

The results of the Western Blot analyses are shown in FIG. 1. Panel A shows the results of Experiment A, panel B shows the result of Experiment B. The supernatants were probed with an anti-GAG antibody or an anti-GPCR antibody as indicated in FIG. 1.

Panel A of FIG. 1 shows that the co-expression of GAG and the GPCR in a host cell transfected with both vectors leads to the excretion of VLPs, as indicated by the presence of a positive GAG band on the Western blot. However, essentially no GPCR is detectable in the VLPs. This confirms that the co-expression of the individual molecules leads to a scenario in which the integration of the GPCR into the VLP only occurs by chance and at a low frequency.

In contrast, Panel B of FIG. 1 shows that the co-expression of GAG and a GPCR-GAG fusion protein leads to a high expression level of GAG and GPCR-GAG in the VLPs. This confirms that the GPCR are efficiently integrated into the VLPs, and that the GPCRs are detectable with antibodies. This means that the GPCR is displayed in a manner that makes it accessible for further molecular manipulation.

Figure 2:
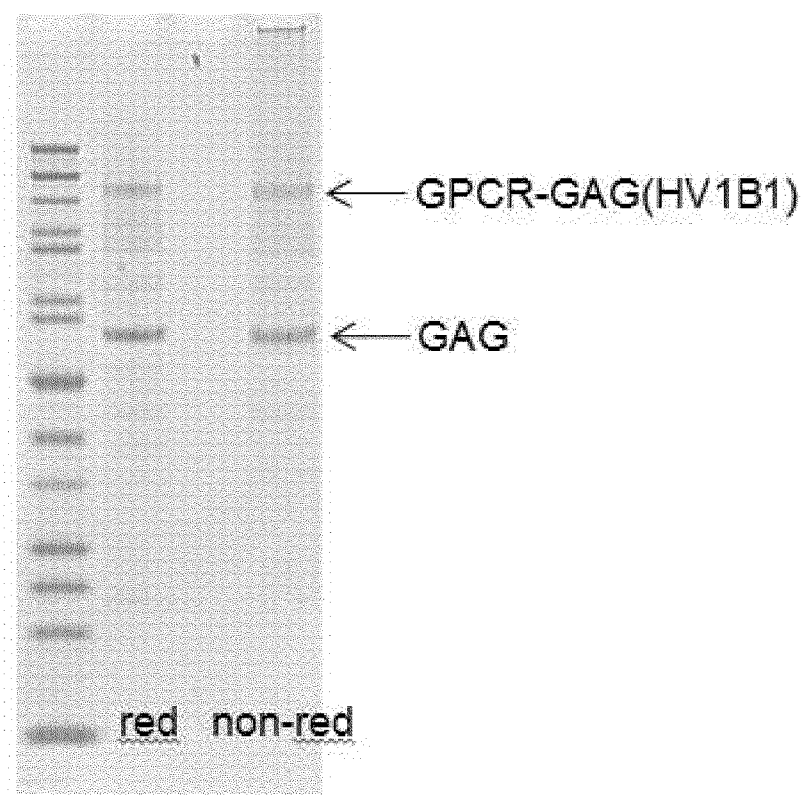
FIG. 2 shows a SDS-PAGE of the VLPs of Experiment B.

FIG. 2 shows a SDS-PAGE of the VLPs of Experiment B. As can be seen, the VLPs essentially consist of two proteins: GAG and the GPCR-GAG fusion protein.

Example 4: Repetition with Additional Integral Membrane Proteins

Examples 1-3 were repeated with two additional GPCR molecules. All results could be confirmed with these additional molecules.

Figure 3:
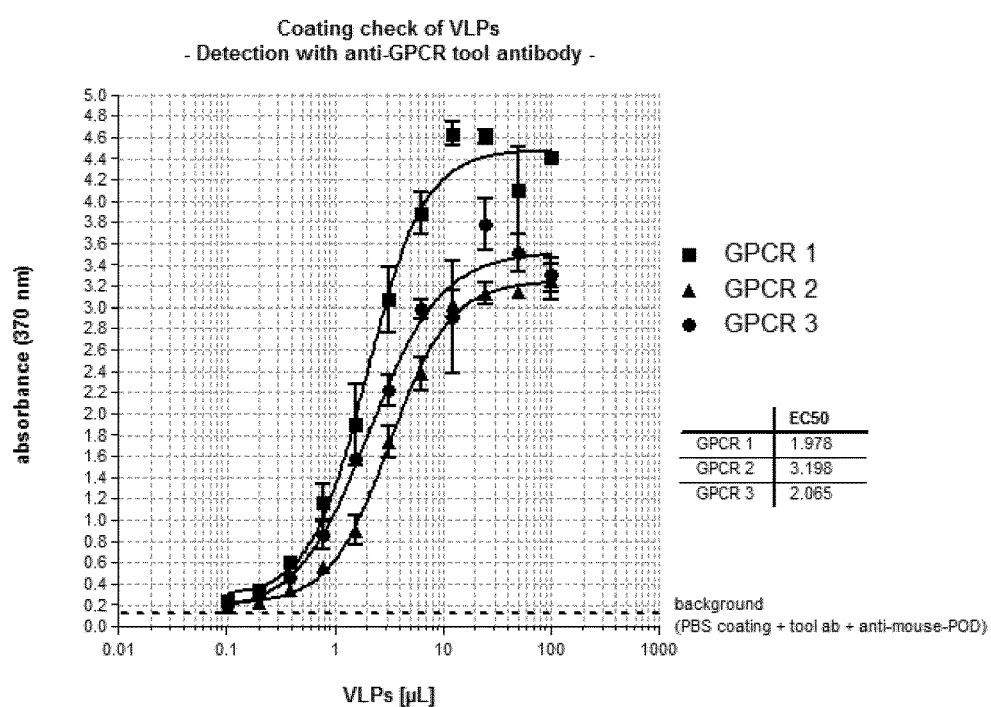
FIG. 3 shows an ELISA experiments with three different GPCR-GAG fusion proteins. Details are given in Example 4.

FIG. 3 shows a comparative analysis of the three GPCRs tested in the present disclosure. As can be seen all three GPCR could be expressed efficiently in the form as GPCR-GAG fusion proteins. Display rates were high enough for standard ELISA measurements.

---

The invention claimed is:

1. A fusion protein comprising a membrane protein N-terminally fused to a retroviral major capsid protein selected from the Gag protein of Moloney murine leukemia virus and the Gag protein of Human immunodeficiency virus.

2. The fusion protein according to claim 1, wherein said fusion protein is capable of being incorporated or encapsulated into virus-like particles.

3. The fusion protein according to claim 1, wherein said membrane protein is a G-protein coupled receptor.

4. The fusion protein according to claim 1, wherein said G-protein coupled receptor is selected from CCR1, CXCR1, CXCR2, CXCR4, CXCR5, CXCR7, motilin, ghrelin, PAR1 and PAR2.

5. The fusion protein according to claim 1, wherein said fusion protein comprises a linker peptide between said membrane protein and said retroviral major capsid protein.

6. A nucleic acid molecule encoding a fusion protein of claim 1.

7. A vector comprising the nucleic acid molecule of claim 6.

8. A host cell containing the nucleic acid molecule of claim 6.

9. A host cell containing the vector of claim 7.

10. A virus-like particle comprising a fusion protein according to claim 1.

11. A virus-like particle according to claim 10, wherein said fusion protein is displayed on the surface of said virus-like particle.

12. A method to identify a binding moiety binding to a membrane protein, said method comprising the steps:
(a) providing a fusion protein according to claim 1,
(b) generating virus-like particles (VLPs) comprising the fusion protein of step (a),
(c) contacting the VLPs of step (b) with an antibody library,
(d) washing the VLPs to remove those antibodies that did not bind the VLP, and
(d) selecting an antibody which is reactive with the membrane protein part of said fusion protein.

* * * * *